United States Patent [19]

Shlain

[11] Patent Number: 5,345,949
[45] Date of Patent: Sep. 13, 1994

[54] METHODS FOR USE IN SURGICAL GASTROPLASTIC PROCEDURE

[76] Inventor: Leonard M. Shlain, 40 Century Dr., Mill Valley, Calif. 94941

[21] Appl. No.: 107,561

[22] Filed: Aug. 20, 1993

Related U.S. Application Data

[63] Continuation-in-part of Ser. No. 939,211, Sep. 2, 1992.

[51] Int. Cl.⁵ .............................................. A61B 19/00
[52] U.S. Cl. .................................. 128/898; 606/157; 604/101
[58] Field of Search ............................ 128/897–898; 606/142–143, 215–216, 219–220, 151, 157, 195; 604/97, 99, 101, 51, 28

[56] References Cited

U.S. PATENT DOCUMENTS

| | | | |
|---|---|---|---|
| 4,696,288 | 9/1987 | Kuzmak et al. | 128/898 |
| 4,803,985 | 2/1989 | Hill | 128/898 X |
| 5,156,609 | 10/1992 | Nakao et al. | 606/142 |
| 5,226,429 | 7/1993 | Kuzmak | 128/898 |

OTHER PUBLICATIONS

Deitel et al.; Vertical Banded Gastroplasty; Canadian Journal of Surgery; vol. 29, No. 5, Sep. 1986; pp. 322–324.

Mason; Vertical Banded Gastroplasty for Obesity; Arch. Surg. vol. 117; May 1982; pp. 701–706.

Willbanks; Long-Term Results of Silicone Elastomer Ring Vert. Gastroplasty for the Treatment of Morbid Obesity; Surgery vol. 101, No. 5; May 1987; pp. 606–610.

Primary Examiner—Angela D. Sykes
Attorney, Agent, or Firm—Townsend and Townsend Khourie and Crew

[57] ABSTRACT

Methods and devices are disclosed for performing laparoscopic gastroplasty for the treatment of morbid obesity. The method utilizes a stapling device or clip and a nasogastric tube for positioning the stapling device. A non-absorbable staple support strip or clip is to form and support a passage between a proximal pouch and a distal region in the stomach.

6 Claims, 8 Drawing Sheets

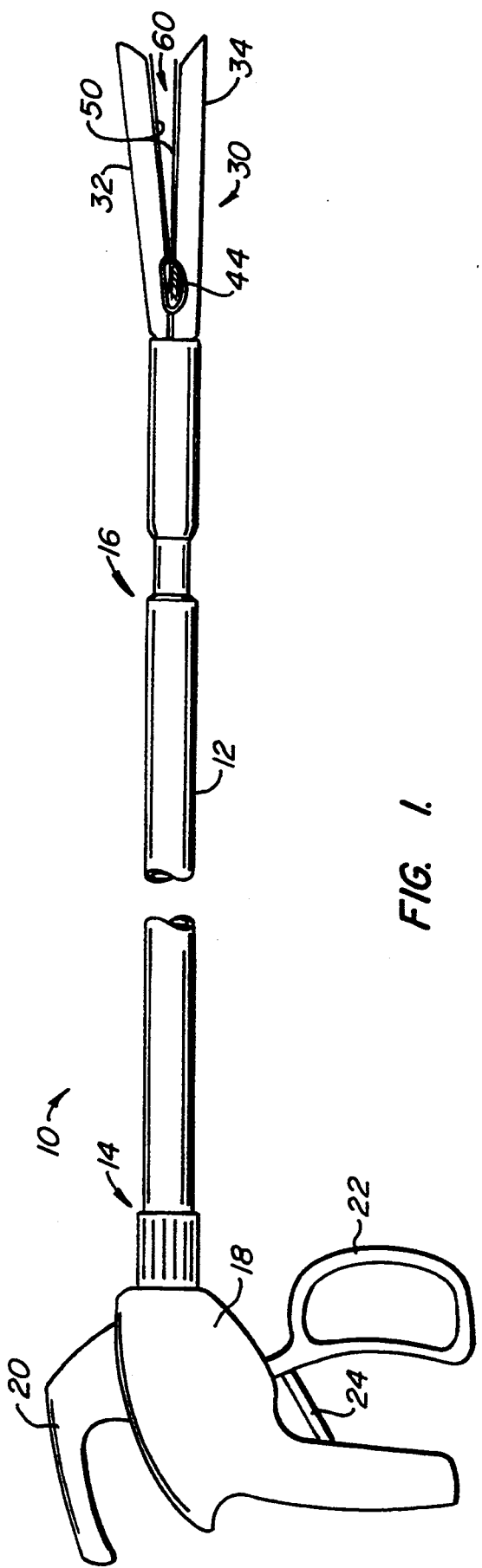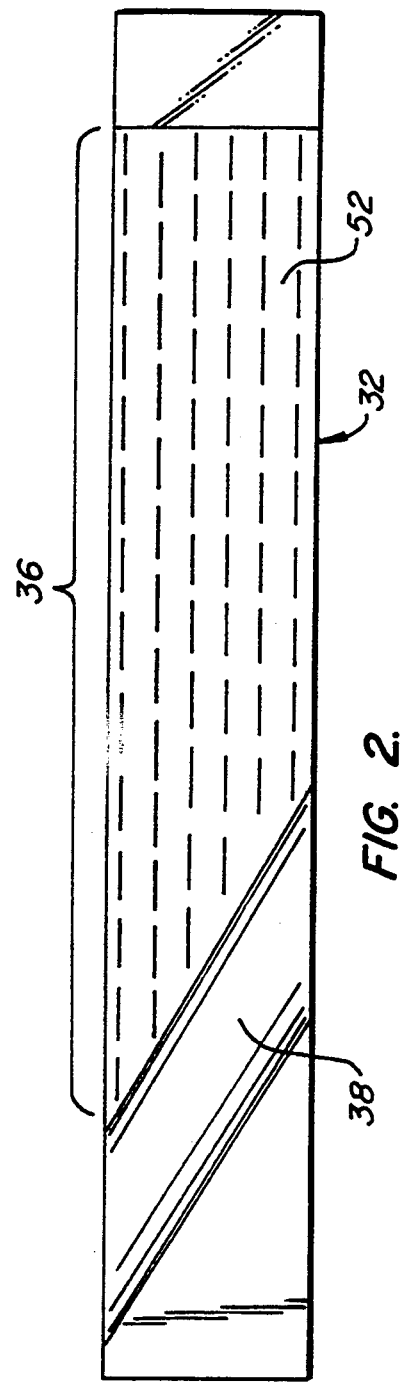

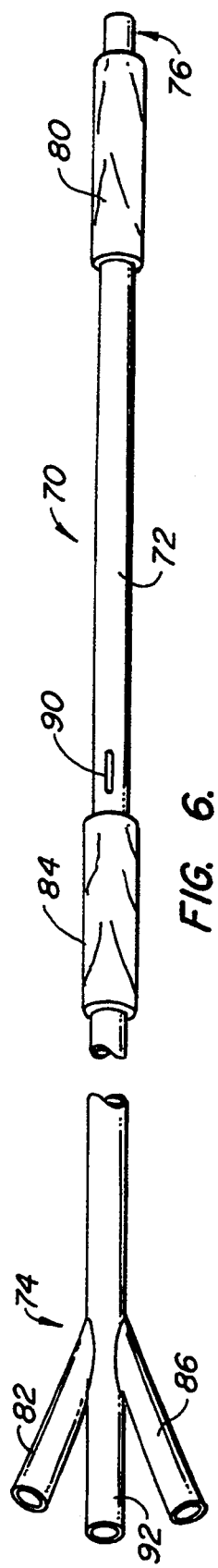
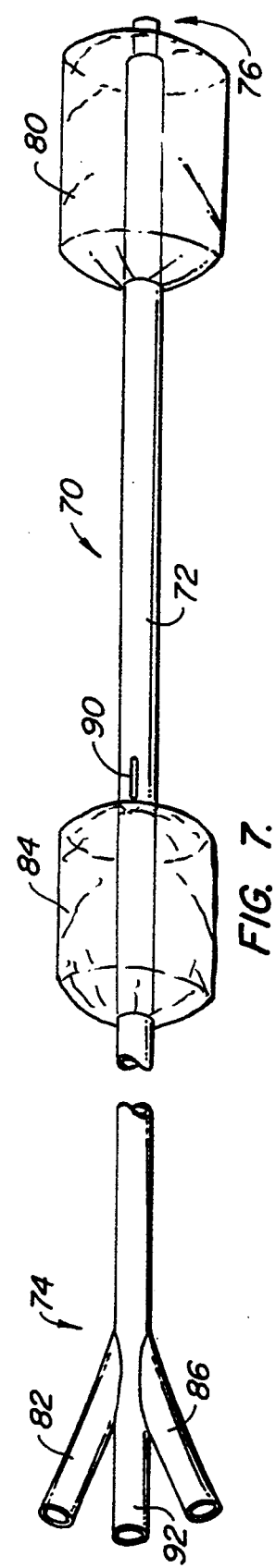
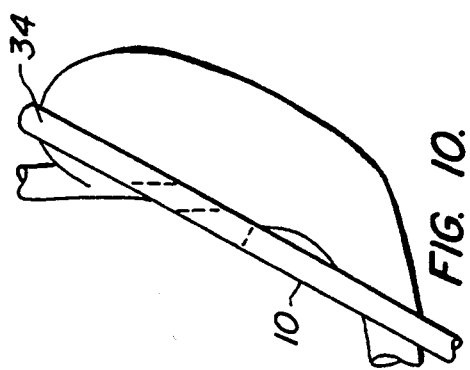
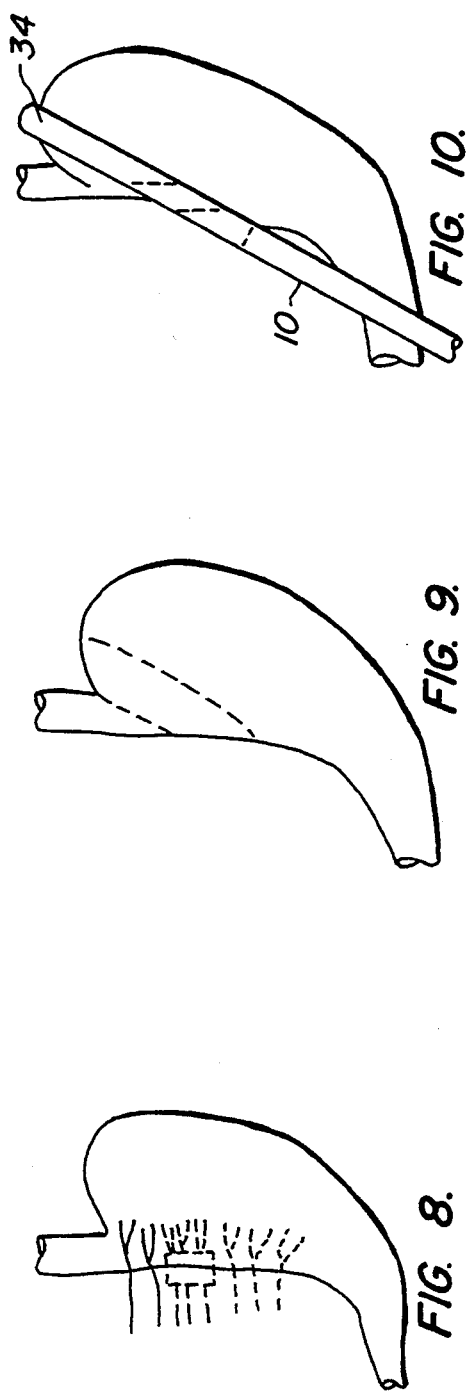
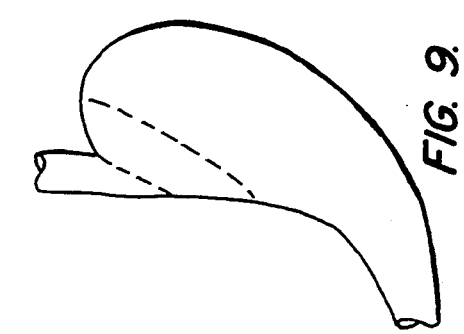

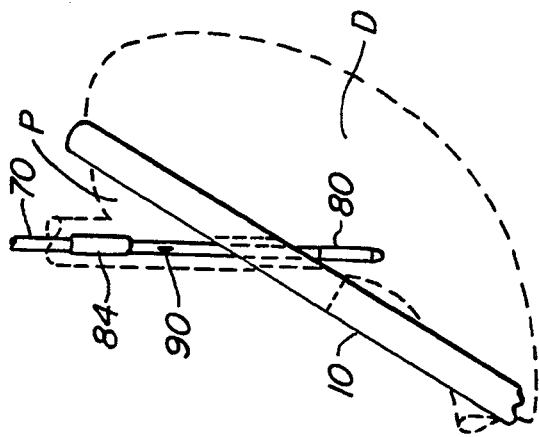
FIG. 11.
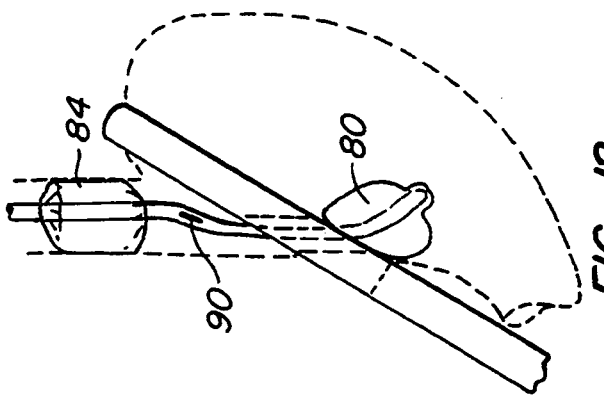
FIG. 12.
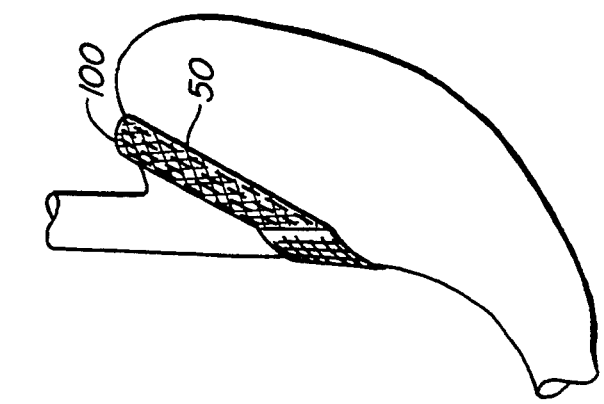
FIG. 13.
FIG. 14.
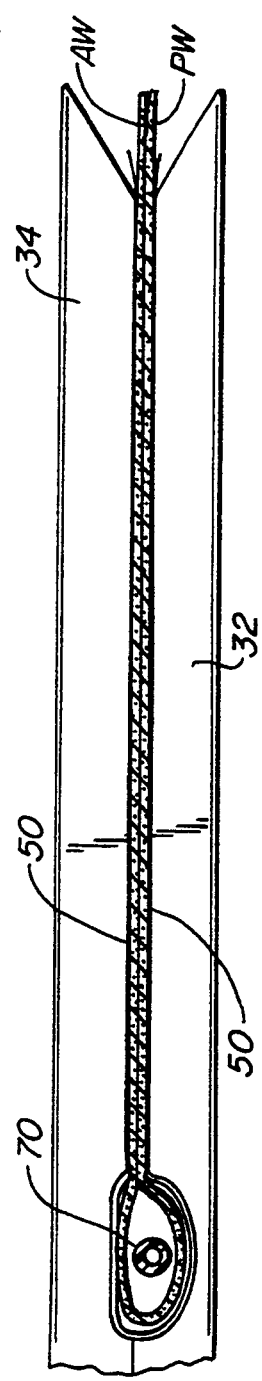
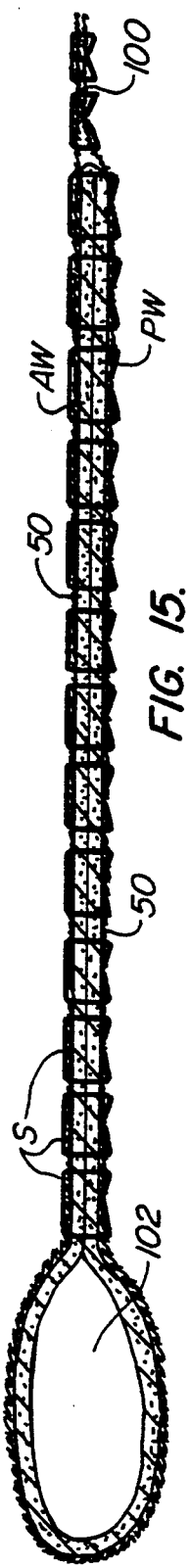
FIG. 15.

METHODS FOR USE IN SURGICAL GASTROPLASTIC PROCEDURE

This application is a continuation-in part of application Ser. No. 07/939,211 filed Sep. 2, 1992, now allowed.

BACKGROUND OF THE INVENTION

1. Field of the Invention

The present invention relates generally to methods and devices for surgically treating obese individuals. More particularly, the present invention relates to a method and device for performing gastroplasty procedures relying on the laparoscopic placement of a vertical band partitioning the individual's stomach.

Obesity is the most frequent nutritional disorder in Western civilization. In the U.S., over 34 million citizens between the ages of 20–75 are overweight, and of those, 12.4 million are morbidly obese, i.e. being 100 pounds over their desirable weight or having one or more serious medical conditions in association with obesity. Such morbid obesity carries with it a greatly enhanced risk of premature death, particularly between the ages of 25–35, where there is a 12-fold increased risk of death compared with the non-obese. The most common causes of death are heart disease, stroke, diabetes mellitus, cancer, pulmonary diseases, and accidents.

Presently there are but two methods of treatment for morbid obesity—diet and surgery. Numerous studies have found diet alone is generally unsuccessful with recidivism rates approaching 95%. After abandoning the highly successful jejunal-ileal bypass surgical procedure performed in the early 70's because of its unacceptably high rate of late metabolic complications, surgeons have developed two different gastric surgical approaches—the Vertical Banded Gastroplasty (hereafter called VBG) and the Gastric Bypass. Each of these procedures has its advantages and disadvantages- The Gastric Bypass, which entails short circuiting the gastric pouch, has previously been more successful in bringing about sustained weight loss. However, the procedure is more difficult to perform, has a higher rate of catastrophic post-operative complications, and produces long term deleterious changes due to the rerouting of the alimentary flow.

Vertical Banded Gastroplasty is more commonly performed than Gastric Bypass because it is simpler, has fewer major complications, and does not disturb normal alimentary continuity. VBG relies on stapling the stomach to create a small partitioned pouch high up in the stomach that can contain no more than 50 ml of food and liquid, where the pouch has a small diameter (typically not exceeding 10.7 mm) controlled non-dilatable outlet to the larger stomach. The smaller pouch which receives food and liquid directly from the esophagus (gullet) will fill quickly. Because the outlet from this smaller pouch into the larger stomach is quite narrow, the patient will experience early satiety, which in turn will decrease the appetite and result in weight loss.

Vertical Banded Gastroplasty is accomplished by accessing the patient's general peritoneal cavity through a very long abdominal incision and an exemplary procedure involves the following steps.

Step 1: The lesser curvature of the stomach is dissected from any attaching structures over a distance of about 3 or 4 cm. This requires clearing all blood vessels and nerves from the anterior and posterior aspects of the stomach.

Step 2: A 32 French Ewald rubber tube is placed through the patient's mouth and into the stomach and is held against the lesser curvature ($32f = 10.7$ mm, this tube calibrates the size of the outlet). A special stapling device called an EEA TM (U.S. Surgical Corporation, Norwalk, Conn.) punctures both gastric walls, then punches-out and seals a 28 mm diameter circle in both walls of the stomach. Thus, a small hole is created in the stomach by stapling the front and back walls of the stomach together.

Step 3: A second stapling device (TA-90B TM, available from U.S. Surgical Corporation, Norwalk, Conn.) is specially designed to place 4 rows of linear staples and is introduced through the stomach hole so that the lower jaw of the staple device is on the back wall of the stomach and the upper jaw of the staple device is on the front wall of the stomach. The length of stomach that needs to be stapled varies from 5-9 cm. The TA-90B TM stapling device is then placed so that its longitudinal axis is parallel to a line from the opening of the esophagus to the new outlet opening constructed next to the punched-out hole. After measuring the proposed volume of the partitioned pouch and making it somewhere between 15 ml and 50 ml, staples in a double row are then fired through both walls of the stomach.

The stomach is now compartmentalized into a smaller proximal pouch which can accommodate only small portions of food. To gain access to the much larger portion of the stomach and the remainder of the digestive tract, food must pass through the narrow exit opening which is the new outlet from the smaller proximal portion of the stomach.

Step 4: The new outlet is encircled with a band of polypropylene non-absorbable mesh which measures 5.5 cm $\times$ 1.5 cm (the mesh resembles a screen door). This band encircling the newly constructed outlet will form a collar. The mesh is placed through the punched-out hole and is secured around the outer surface of the outlet. The mesh, once sutured to itself, prevents the inner diameter of the outlet of the stomach from stretching beyond is initial diameter.

Thus, the steps of the VBG procedure compartmentalize the stomach into a larger portion and a smaller portion. The smaller portion is vertically stapled and its outlet banded with a piece of non-absorbable mesh to insure that it will not increase in size. The smaller pouch will hold a volume of 15–50 ml, and the exit opening, by virtue of its being banded, will not increase in diameter. Such features serve to insure that the patient who attempts to eat too much, too fast will have early satiety, and not overeat.

While this procedure has been successful, it suffers from the fact that obese patients are poor surgical risks. The surgery requires a very long incision, extending through an extremely thick layer of fat. Post-operative healing of such incisions is highly problematic. The procedure is difficult for the surgeon to perform because of the poor exposure associated with the enormous size of these patients.

With the exception of a few centers, VBG has fallen into disuse because of the difficulties associated with the performance of the procedure and the high rate of complications that ensue afterwards. Early complications, such as wound infection, pulmonary emboli, gastric perforation, and subphrenic abscess, are serious and the early mortality figure in the best series runs between 1-3%. Many early complications necessitate reoperation.

Late compilations, such as ventral (incisional) hernias and gallbladder stones, also occur. The most troubling late complication is a disruption of the vertical linear rows of staples. When this occurs, the smaller partitioned stomach now has two openings into the larger stomach and the benefits of the procedure are immediately negated.

In recent years, less invasive surgical (LIS) techniques, such as laparoscopic, thoracoscopic, and arthroscopic techniques, have been performed through small incisions. Such LIS procedures use specialized instruments to carry out the desired surgical result. For abdominal surgery, the specialized instruments are usually introduced through a tube, such as a trocar, while the surgeon observes the manipulation of the instruments through a laparoscope. The image is transmitted by means of a camera attached to the laparoscope to a visual monitor. LIS techniques offer significant advantages over conventional "open" surgical procedures. In particular, the LIS techniques are generally much less traumatic, require substantially shorter recovery periods, and are less costly than corresponding, conventional surgical techniques such as open abdominal surgery.

Accordingly, it would be desirable to provide methods and devices for laparoscopically performing gastroplasty procedures. Such laparoscopic gastroplasty procedures would lessen or avoid the morbidity associated with open surgical gastroplasty procedures. Further, it would be advantageous to perform gastroplasty procedures in a manner that reduced the possibility of staple disruption.

2. Description of Background Art

Surgical gastroplasty procedures are described in Mason (1982) *Arch. Surg.* 117:701-706; Willibanks (1986) *Surg.* 101:606-610; and Deitel et. al. (1986) 29:322-324. Willibanks (1986) illustrates the TA-90 ™ surgical stapling device manufactured by U.S. Surgical Corporation, as described above. A gastroplasty method employing a specialized clamp having an aperture to define the small diameter flow passage between the partitioned portions of the stomach is described in U.S. Pat. No. 4,803,985. A laparoscopic stapling device is described in U.S. Pat. No. 5,040,715, the full disclosure of which is incorporated herein by reference. U.S. Pat. No. 4,802,614 discloses a surgical stapling device with features similar to the model TA-90 ™ manufactured by U.S. Surgical Corporation.

SUMMARY OF THE INVENTION

The present invention relates to a method for performing laparoscopic surgical gastroplasty and devices for use in such procedures. When surgery is performed in this manner, the morbidity associated with an open procedure is reduced or avoided.

A method and related apparatus for performing laparoscopic gastroplasty on a patient includes percutaneously introducing a plurality of trocars through the patient's abdominal wall in place of an abdomen opening incision. Visualization of the patient's stomach using a laparoscope disposed in one of the trocars is utilized. The stomach is surgically prepared and manipulated to expose the walls of the stomach for placement of a band which will partition the stomach into two compartments with an opening between them. Specifically the stomach is dissected from the surrounding mesentery along a line dividing the stomach into a proximal pouch adjacent the esophagus and a distal region. A banding device is introduced and positioned to bring the walls of the stomach adjacent to one another between the proximal pouch and the distal region of the stomach. The banding device defines an aperture for permitting flow from the proximal pouch to the distal pouch. A nasogastric tube is introduced into the stomach so that it passes through the aperture in the band device. A first balloon is inflated on the nasogastric tube distally of the aperture to close the proximal pouch. A second balloon is inflated in the esophagus, causing the proximal pouch in the stomach to be sealed. A measured volume of fluid is injected through the naso-gastric port into the proximal pouch through the nasogastric tube until the pouch is filled and the pouch sized. The banding device is repositioned until the position of the banding device provides a preselected fluid volume to the operative defined pouch upon filling. Thereafter, the banding device is radially fastened around the stomach with sufficient force to bring the opposing walls of the stomach together to divide the proximal pouch from the anterior portion of the stomach. The banding device is thereafter stapled at least to the superficial walls of the stomach or otherwise fastened to the stomach to prevent migration. The banding device at its final position, produces a proximal pouch with diminished volume to produce early patient satiation upon eating for surgically induced obesity control with a passage between the proximal pouch and distal region of the stomach being defined by the aperture for nutrients.

The present invention overcomes many of the disadvantages of obesity-related surgery discussed above. Laparoscopy is utilized negating abdomen opening incision.

Two types of banding devices and related surgical procedures are set forth. The first banding device is a strip for providing the aperture and stapling the walls of the stomach one to another. The second banding device is a clamp having opposed portions for bringing the walls of the stomach in sealing contact with one another and defining the required aperture.

In the stapled band embodiment, a laparoscopic stapling device is provided which in a single step can effect both (1) vertical stapling partition of a stomach and (2) banding of the stomal outlet. By employing a nonabsorbable tissue supporting material beneath the staples, surgical failures associated with disruption of the staple line will be decreased.

Two specialized devices are employed in the stapled banding device and related surgical method of the present invention. First, a laparoscopic stapling device provides a means for applying a substantially linear array of staples. The stapler includes a fastening head comprising a housing, or upper jaw, that has a means for mounting surgical staples. The staples will be stored in, and subsequently ejected from, the housing. The housing provides for firing of the staples from a region substantially at the distal end of the housing, to a position spaced distally from the proximal end of the housing. The fastening head also includes an anvil, or lower jaw, that defines a surgical staple guiding surface. The anvil is pivotally mounted relative to the housing so that the anvil and housing can move between an open and a closed position. The closed position will further include a cocked position and a fire position, as described in more detail below. The fastening head will have a tissue contacting surface that extends along the housing and anvil. When the anvil and housing are in the open position, sufficient space is provided to allow positioning of the anvil and housing on opposite sides of a human stomach. When the anvil and housing are in a closed position, they define an aperture near their respective proximal ends, in the region where staples are not fired. The aperture defined by the anvil and housing will generally have a longitudinal axis oriented from between 20° to 50° relative to the longitudinal axis of the fastening head, with a diameter selected to provide a desired cross-sectional area for the outlet passage between the divided portions of the stomach, as discussed below.

The housing and anvil of the fastening head will typically carry a thin non-absorbable support strip that covers the tissue contacting surface. This non-absorbable support strip is preferably a continuous length of mesh material which defines the non-absorbable tissue supporting material between the staples and the tissue after the staples have been secured in the stomach wall.

Second, a nasogastric tubular device having proximal and distal ends comprises an access port, a first tubular portion, a first balloon, a second tubular portion, and a second balloon located substantially near the distal end of the device. The second tubular portion of the device may have an emission port. Separate lumens can connect the distal balloon, the emission port, and the proximal balloon to the access port at the proximal end of the device.

The stapled banding procedure of the present invention is carried-out laparoscopically, although the devices might also find use in conventional open-surgical methods. Accordingly, the method of the present invention comprises laparoscopically accessing the stomach and then stapling the stomach in a manner which forms the stomach into proximal and distal chambers having a reduced-size passage therebetween. After the stomach is accessed, it is manipulated to facilitate placement of the staple device along a generally desired dividing line. Thereafter, the nasogastric tube of the present invention is introduced through the mouth and throat to help in accurately positioning the stapling device to provide the desired capacity of the proximal stomach chamber. The stapling device is cocked to the compressed walls of the stomach, with the second tubular portion of the nasogastric tube passing through the region of the stomach located within the aperture of the stapling device. The emission port of the second tubular portion is located proximal to the aperture, and the distal balloon of the tube is located on the distal side of the stapling device. The proximal and distal balloon of the tube are inflated with the proximal balloon occluding the distal end of the esophagus. A quantity of solution is introduced to the tube and flows into the proximal portion (pouch) of the stomach via the emission port. Preferably, the amount of fluid introduced will be approximately 15–50 mm (the desired final volume of the proximal pouch of the stomach after stapling). Thereafter, the stapling device will be fired to position and close a line of staples (engaging both the front and back of the support strip described above) to form the proximal stomach chamber having the desired capacity.

In the clamp device and procedure, an especially designed clamp is utilized for enabling trocar introduction, laparoscopic banding of the stomach, and conventional stapling which is not through and through stapling. The function of these staples is to prevent migration of the clamp. The clamp includes posterior and anterior portions connected at one end by a hinge and at the opposite end by a fastening device, preferably screw and wing nut attached to the posterior portion for fastening and threading to a receiving opening in the anterior portion. Medially of both the anterior portion and posterior portion, the stomach contacting clamp sides are interrupted and have fastened at their point of interruption elastic arches spanning the interruption. These elastic arches define the required stomach aperture and have a flexible arcuate strip underlying the elastic arches to permit formation of the underlying aperture once the clamp is applied to the stomach. The elastic arches also impart sufficient flexibility to the posterior and anterior clamp sides for trocar introduction. Both clamp sides are provided with windows for exposing the underlying stomach wall between the top and bottom portions of the clamp. These windows allow state of the art pulse oximeter monitoring or Doppler blood flow of the stomach walls to remotely measure arterial blood flow during clamp installation for precision tightening of the clamp during installation. Finally, the anterior portion of the clamp includes woven mesh material extending above and below the clamp which enables superficial stapling of the clamp in place against unwanted migration.

A method for performing laparoscopic gastroplasty on a patient utilizing the clamp device includes percutaneously introducing a plurality of trocars through the patient's abdominal wall in place of an abdomen opening incision. As before, visualization of the patient's stomach using a laparoscope disposed in one of the trocars is utilized. Again and as before, the stomach is dissected from its mesentery along a line dividing the stomach into a proximal pouch adjacent the esophagus and a distal region. A pliable catheter is threaded in an entrance trocar, around the posterior portion of the stomach and threaded out an exit trocar. At the exit trocar, the clamp—preferably in the closed position—is fastened typically at the wing nut of the posterior portion. Thereafter, the clamp is drawn by the tube until the posterior portion is behind the stomach. Once the posterior portion of the clamp is in place behind the stomach, the anterior portion is folded over the stomach to close the clamp with the wing nut and notch holding the clamp generally closed for defining the proximal pouch. As before, the nasogastric tubular device is utilized to size the pouch and manipulate the clamp to define the required size proximal pouch. Once the correct size of pouch is determined, the clamp is closed and tightened utilizing a pulse oximeter or Doppler device to measure stomach wall arterial blood flow to gauge correct clamp tightness. Finally, stapling of the anterior clamp portion attached mesh to the anterior portion of the stomach occurs. This latter procedure assures that migration of the clamp does not occur.

At least three distinctions over similar clamp type devices and procedures found in the prior art are present. First, this application is for laparoscopic insertion (although it could be used just as well in an open procedure). Secondly, by stapling the mesh coming off the top and bottom portions of the anterior jaw of the clip provide a means to prevent the disclosed clip from migrating; the prior art does not disclose a mechanism to prevent this from occurring. Finally, by using a sensing device to determine blood flow, my invention would prevent tissue necrosis. The disclosed screw-thread clasp in combination with the windows for arterial blood monitoring will give the surgeon the ability to adjust the tightness of the clip while at the same time measuring blood flow to make sure the gastric wall is being nourished.

BRIEF DESCRIPTION OF THE DRAWINGS

FIG. 1 is a side, elevation view of a laparoscopic stapling device employing the specialized fastening head of the present invention.

FIG. 2 illustrates the tissue-contacting surface of the staple housing of the fastening head of the stapling device of FIG. 1.

FIG. 6 illustrates the nasogastric tube of the present invention, with its first and second balloons deflated.

FIG. 7 illustrates the nasogastric tube of FIG. 6, with its first and second balloons inflated.

FIGS. 8–12 and 14 illustrate the stomach of an individual undergoing a laparoscopic gastroplasty procedure according to the method of the present invention.

FIG. 13 illustrates the fastening head of the surgical stapling device with a portion of the patient's stomach wall therein, with the passage between the distal and proximal divided portions of the stomach being illustrated.

FIG. 15 is a cross-sectional view of the portion of stomach which has been stapled according to the method of the present invention using the stapling device of the present invention, with a plurality of individual staples and strip of tissue supporting material in place.

DESCRIPTION OF THE SPECIFIC EMBODIMENTS

Figure 3:
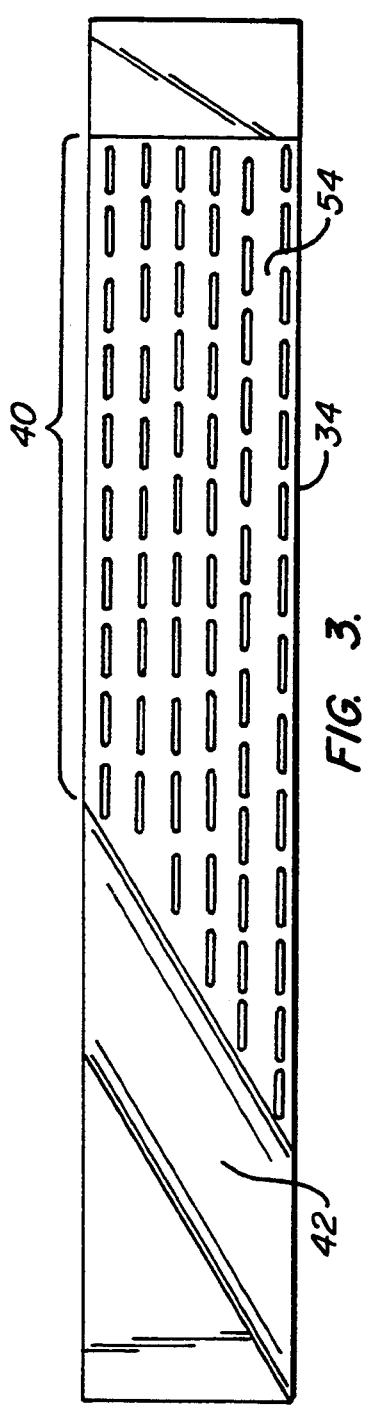
FIG. 3 illustrates the tissue-contacting surface of the anvil of the fastening head of the surgical stapling device of FIG. 1.
Figure 4:
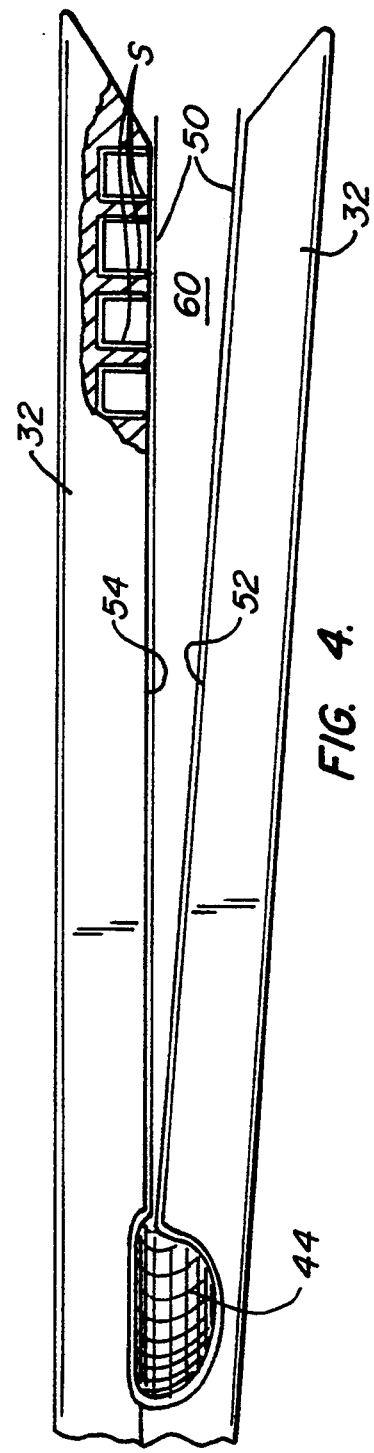
FIG. 4 is a detailed side view of the fastening head of the surgical stapling device of FIG. 1, with portions broken away, shown in its open, tissue-receiving configuration.
Figure 5:
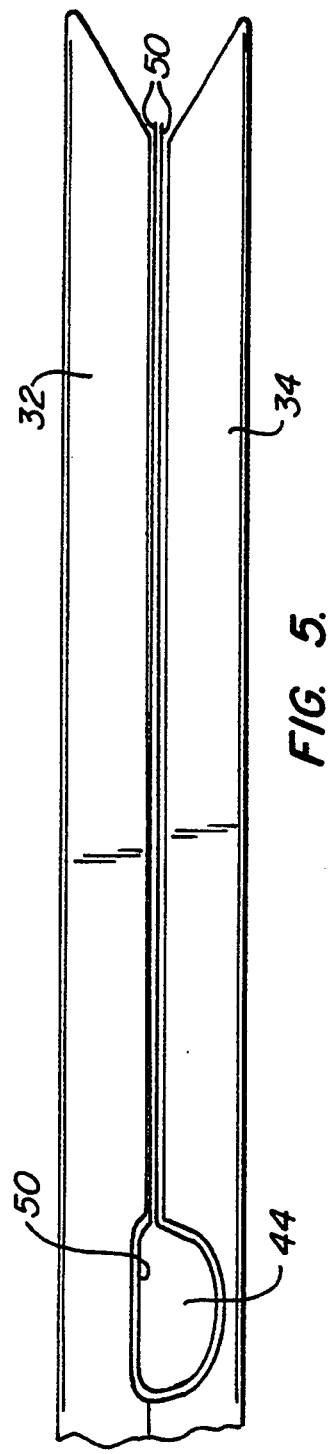
FIG. 5 is a detailed view of the fastening head of the surgical stapling device of FIG. 1, similar to FIG. 4, except that the housing and anvil are closed together in the stapling configuration.

According to the method of the present invention, a gastroplasty procedure is performed laparoscopically. Two specialized instruments are utilized that facilitate laparoscopic gastroplasty. However, these devices can be used in an open surgical procedure as well.

The first specialized device is a stapling device 10 (FIGS. 1–5) which includes an endoscopic tube 12 having a proximal end 14 and a distal end 16. A handle 18 is rotatably attached to the proximal end 14 of the endoscopic tube 12 and includes a cocking lever 20 and a firing trigger 22. A locking latch 24 is further provided in order to prevent accidental firing of the staples, as will be described in more detail hereinafter.

The stapling device 10 further includes a fastening head 30 at its distal end, with the fastening head including a housing 32 (upper jaw) which carries a plurality of rows of staples and an anvil 34 (lower jaw) which acts to close the staples after they are ejected from the housing using the trigger 22. The cocking handle 20 may be moved up and down in order to open and close the anvil 34 against the housing 32.

As thus far described, the stapling device 10 is constructed and will effect stapling in the manner of the commercially available laparoscopic Endo-GIA ™ stapling device, available from U.S. Surgical Corp., Norwalk, Conn. The stapling device 10 of the present invention, however, must be modified to include features not present in previous stapling devices.

In particular, the fastening head 30 of the stapling device 10 of the present invention must include a specialized housing 32 and a specialized anvil 34, as best illustrated in FIGS. 2–5. The housing 32 and anvil 34 will each be sufficiently long to staple the desired partition in the stomach, usually being approximately 8 cm to 12 cm in length, preferably being about 9 cm in length. The housing 32 has a staple storing region 36, and a depression 38 that lacks staples. The anvil 34 has staple guiding surfaces 40, and a depression 42 which will align with depression 38 in housing 32 to form an aperture 44 (FIGS. 4 and 5), which defines the passage between the partitioned portions of the stomach, as described hereafter. The staple guiding surface 40 cause B-shaped bending of the staples when the fastening head 30 of the device 10 is closed and fired.

Of particular importance to the present invention a staple support strip 50 (FIGS. 1, 4, and 5) will be carried along the inner, tissue-contacting surfaces 52 of both the housing 32 and anvil 34, as well as over the surfaces of the depressions 38 and 42. The strip 50 is formed continuously so that when the anvil 34 is closed against the housing 32, and the staples S are fired, the staples will firmly attach the adjacent portions of the staple support strip 50 together, as well as any tissue which may have been between the opposed portions of the support strip when the staples were fired. As the depressions 38 and 42 are free from staples, however, the support strip 50 will maintain an enlarged passage through the region which was located in the depressions at the time of firing.

The tissue support strip 50 may be any biologically compatible material having sufficient strength to act as backing for the staples S and to define a fixed aperture diameter for the connecting region between the proximal and distal portions of the stomach, as described in more detail hereinafter. A preferred tissue support strip material is a polymeric mesh, with a particularly preferred material being Marlex ™, available from Ethicon Corporation, New Brunswick, N.J.

When open (FIGS. 1 and 4), the fastening head 30 defines an open region 60 that is sufficient in size so that the housing 32 and anvil 34 can be positioned on opposite sides of a human stomach. When the fastening head 30 of the stapling device 10 is closed (FIG. 5), the housing depression 38 and anvil depression 42 define the aperture 44, which leaves the only passage between the proximal and distal portions of the stomach after stapling. Preferably the aperture will be ovoid in cross section. The preferred oval shape of the aperture allows the stapling device to have a smaller overall diameter. The aperture 44 will be oriented at an acute angle of between 20° and 50°, and most preferably is approximately 30° relative to the longitudinal axis of the fastening head 31. The angle of aperture 44 is necessary in order to properly orient the passage between the proximal and the distal portions of a patient's stomach when the fastening head 30 is introduced from a typical laparoscopic access direction. That is, it will be difficult or impossible to orient the stapling device 10 itself in order to achieve the desired angle, so the angle is preset into the fastening head to facilitate use.

The device 10 of the present invention will typically be longer than conventional laparoscopic stapling devices of the prior art, to accommodate the increased girth of the patients. Preferably, the device is at least 50 cm in length often being longer. Preferably, the device will also have an articulated fastening head allowing up to 30° or more of lateral deflection.

The second specialized device utilized in the surgical gastroplasty methods of the present invention is a nasogastric tube 70, as illustrated in FIGS. 6 and 7. The tube is used in conjunction with the stapling device 10 of the present invention in order to properly position the line of staples which is being discharged by the stapler. This tube 70 will be constructed of materials, and by methods known to those in the art, typically being formed by the extrusion of polymeric materials, such as polyethylene, PET, PVC, and the like.

The nasogastric tube 70 includes flexible tube body 72 having a proximal end 74 and a distal end 76. The main portion of body 72 will have an outer diameter in the range from about 6 to 9 mm, preferably being from about 6 to 9 mm, although the diameter is not critical. A first, distal balloon 80 is formed near the distal end of body 72 and is connected to inflation lumen 82 at the proximal end of tube 70. A second, proximal balloon 84 is located proximally of the distal balloon, typically being spaced from the distal balloon by a distance in the range from about 6 cm to 10 cm, usually from about 6 cm to 10 cm. The proximal balloon 84 is inflatable through lumen 86 located at the proximal end of the tube 70. An emission port 90 is formed in the body 72 and disposed between the balloons 80 and 84, preferably lying just distally of the proximal balloon 84. Emission port 90 is connected to lumen 92 at the proximal end of the tube 70, allowing the user to introduce a fluid into a region defined between the inflated balloons 80 and 84, as illustrated in FIGS. 7 and 12.

The diameter of tube 70 between the balloons 80 and 84 will be selected to help define the diameter of the passage which is being created between the proximal pouch and distal region of the stomach. Typically, the diameter will be between 6 mm and 15 mm, more usually between 6 mm and 9 mm, and most usually being about 6 mm.

Preferably, the steps involved in laparoscopically performing this operation, utilizing the newly described devices, are as follows.

Step 1: The patient is prepared for surgery in the usual manner. A foot board is placed to allow the patient to be placed in a head up position.

Step 2: After the patient is anesthetized, and pneumoperitoneum is obtained in the standard fashion, trocars are placed as they would be for any laparoscopic gastric procedure, with a 15 mm port usually being necessary for the introduction of the stapling device 10. Typically, four trocars are needed: A right lateral upper quadrant trocar for liver retraction, a 10 mm umbilical port for a 0 to 45 degree straight laparoscope, a 15 mm operating port in the right upper quadrant, and a 10 mm port in left upper quadrant.

Step 3: The surgeon next manipulates the stomach so as to visualize the vessels on the stomach wall. Preferably, a intragastric manipulating device will be used, where the device is introduced orally and manipulated from its proximal end. The manipulating device will typically include means for attaching to tissue located at its distal end. The means for attaching to tissue usually includes a vacuum attachment head which may be reciprocally positionable within and out of a lumen at the distal end of the device.

Manipulating movements achievable by the intragastric manipulating include the ability to deflect the distal end of the device up to about 270° from the longitudinal axis; the ability to move the device up to about 45° from the longitudinal axis at a location intermediate of the proximal and distal ends of the device; and the ability to move the device up to about 180° rotatably, relative to the longitudinal axis of the device, the rotatable movement occurring at a location intermediate of the proximal and distal device ends.

By use of such a intragastric manipulating device, the surgeon may effectively manipulate the stomach from the inside instead of by grasping and retracting the stomach from the outside in order to visualize vessels on its wall and to carry out vaso-occlusion.

Step 4: With the stomach retracted laterally, the vessels of the lesser curvature are stretched. Using a microscissor (Endoshears ™; USSC Norwalk, Conn.), the peritoneum is incised along the lesser curvature of the stomach for a distance of 2–3 cm. This dissection is performed at a site approximately 4–5 cm distal to the incisura (the junction between the lateral side of the esophagus and the stomach and just above the crow's feet of the Nerve of Latarjet). See FIGS. 8 and 9. Vaso-occlusion after ligation of the vessels on the stomach wall is accomplished with knot tying, and clipping. During vessel ligation, care is taken to not disturb the anterior nerve of Latarjet.

Step 5: The stomach is then rotated to bring the posterior wall of the lesser curvature into view, allowing the surgeon to continue the ligation and clipping of the vessels that enter on the posterior wall of the lesser curvature. Accordingly, a passage will be created along the lesser curvature and along the posterior wall of the stomach. Preferably, the intragastric manipulating device used in Step 3, will be utilized to facilitate stomach manipulation and vaso-occlusion.

Step 6: An flexible endoscope, such as that commercially available from Olympus (Olympus Corporation, Lake Success, N.Y.) is then gently inserted through the 15 mm trocar and insinuated along the posterior wall of the stomach, through the passage being created between the divided blood vessels of the lesser curvature. Endoscopic visualization permits the surgeon to determine if any vessels have not been ligated. Should further ligation be necessary, the process of ligation and vaso-occlusion as set forth in Step 5 is continued. Preferably, the manipulating device described in Step 3 is positioned within the stomach and used to elevate the stomach toward the anterior abdominal wall while the endoscope is being inserted. Should the stomach be manipulated with such an intragastric device, the lesser sac behind the stomach is exposed, while also stretching the peritoneal reflection as well as any aberrant posterior gastric blood vessels.

Preferably, the endoscope is advanced using flexible dissecting instruments to clear a path. Any vascular adhesions or non-dissected peritoneum would preferably be cut using the flexible scissors. Adhesions containing small blood vessels would be grasped and cauterized utilizing methods and devices known to those of skill in the art. If a significant blood vessel should be encountered, a flexible clip applier would preferably be introduced and clips placed on the vessel both proximally and distally. A flexible scissor would then be introduced and used to divide the vessel between the clips. In the event that troublesome bleeding should occur in this relatively inaccessible area, injection of fibrin glue should control the bleeding. As is known in the art, pre-operative preparation would have included the preparation of fibrin glue made from the patient's own blood products.

The flexible endoscope is advanced into the free space behind the stomach until it emerges at the incisura (the junction between the lateral side of the esophagus and the stomach). The light from the endoscope is visualized during this maneuver by means of the laparoscope that is in place through the umbilicus. (Solos Corp., Atlanta, Ga.).

When the flexible endoscope arrives at the upper end of the space behind the stomach, it will be seen through the peritoneum that attaches the stomach to the diaphragm. This peritoneal veil could be broken through from below, using the flexible endoscope. Alternatively, dissection of this peritoneal veil could be carried out from above by observing with the laparoscope and clearing away any blood vessels and tissue veils in this relatively avascular plane, utilizing procedures and methods known to those of skill in the art. Thus, a passage is created along the posterior wall of the stomach on the lesser curvature side while insuring that disadvantageous bleeding does not occur.

Step 7: The stapling device 10 (FIGS. 10–12) is then introduced through a trocar, and the anvil 34 of the instrument is placed into the tunnel (shown in broken line in FIG. 9) created behind the stomach guided by a rubber tubing previously placed in the tunnel and attached to the housing of the stapling device.

Step 8: Once the anvil 34 of the stapling device 10 is visualized emerging from the gastro-esophageal junction, the surgeon closes the fastening head 30 of the stapling device (FIG. 10), thereby compressing the anterior and posterior walls of the stomach. The specialized nasogastric tube 70 is then inserted into the stomach and observed to pass through the stomach opening delimited by the aperture of the stapling device (aligned beneath the esophagus). See FIGS. 11 and 12. The tube 70 is passed into the distal region of the stomach under direct vision with the laparoscope. It will be seen as a protrusion proceeding along the stomach wall. A portion of the stomach compressed within the aperture 40 of the stapling device 10 and around the distal portion of the nasogastric tube, will be the future outlet of the partitioned stomach. When the nasogastric tube 70 is positioned within the stapling device 10, the typically round outer shape of the second tubular portion would be flattened into an oval, conforming with the preferred shape of the aperture of the stapling device.

Step 9: The distal balloon 80 of the tube 70 is inflated, and the surgeon pulls this balloon proximally thereby cinching the balloon against the opening delimited by the aperture 40 of the stapling device 10. Cinching the balloon 80 in this manner prevents loss of fluid from the proximal portion P of the stomach.

Step 10: The proximal balloon 84 is then inflated, and its position in the esophagus observed under direct vision with the laparoscope. See FIG. 12.

Step 11: The proximal chamber P of the stomach is then filled with a measured amount of saline solution. Preferably, the proximal chamber of the stomach will hold between 15–50 ml of solution. The stomach is usually filled by introducing fluid into the lumen 92 of the nasogastric tube 70 that leads to the emission port 90 located proximate the balloon 84. In the event that the proximal portion of the stomach is too large or too small, the surgeon can open the fastening head 30 of the stapling device 10 and reposition the head, repeating the procedure of this Step until satisfied with the size of the proposed proximal gastric pouch P.

Step 12: The safety release 24 is taken off the stapling device 10, and the device then fired. As is known to those skilled in the art, this would activate pusher bars to eject multiple rows of staples from the housing 32 of the instrument. These staples would emerge from the housing, pass through the support strip 50, pass through the anterior wall AW of the stomach, pass through the posterior wall PW of the stomach, through the support strip on the anvil 34 of the stapling device, then striking the posterior jaw or anvil 34 of the device. Upon striking the anvil 34, the staples S would form into a B shape, locking and making a sandwich of the anterior mesh portion, the anterior and posterior stomach walls, and the posterior mesh portion, as illustrated in FIGS. 14 and 15.

Since the distal end of both jaws of stapling device will preferably extend beyond the stomach of the esophagogastric junction, the staples at the distal-most end of the stapling device will not engage the stomach. These staples would fire through the two layers of mesh only, forming a fastened tail 100 which serves to ensure that disruption of the staple line at this edge will not occur.

When the stapling device 10 has been fired, and the stapling device and nasogastric tube 70 removed, the flattened oval portion of the stomach formerly located between the stapling device and the tube and compressed into an oval shape will regain its circular shape, preferably having the optimum 10.7 mm outlet configuration (102 in FIG. 15) and will be banded by the mesh 50 that lined the stapling device 10.

Step 13: The surgeon withdraws the stapling device 10, and after irrigation removes the instruments and trocars, and closes the skin incisions in a standard fashion. Postoperative care can be simplified by leaving the double lumen tube in place overnight to lessen complications attendant to swelling and bleeding. Ideally, the patient will be sent home the following morning on a clear liquid diet.

FIGS. 16A through 35 illustrate the second embodiment of banding the stomach utilizing a clamp type device 100. The concept is to band the stomach externally with a clip dividing it into two chambers. Referring to FIGS. 16A–16D and 17, the clip 100 is placed horizontally high across the fundus of the stomach. The inlet chamber or proximal pouch will be restricted to 30–50 cc of capacity. Through the center of the rigid clip there is a controlled opening 102 that allows food to pass between the two chambers. This opening is banded with biologically insert non-absorbable mesh 104, 105 to prevent stretching and the diameter of the mesh permanently regulates the size of the outlet preventing it from enlarging. Arches of semi-rigid plastic 108, 109 over the opening maintain the integrity of the clip's design.

Such a clip 100 accomplishes the two goals of the vertical banded gastroplasty operation: a small ante chamber and a controlled outlet. By providing external support instead of relying on through and through staples, clip 100 avoids staple line breakdown which has been the principle reason this operation has fallen into disrepute.

As will hereinafter be more fully set forth with respect to FIGS. 18 through 35, clip 100 is inserted down a trocar, preferably in the closed position. Once in the abdomen, the posterior jaw of the clip is guided into place by affixing its leading edge to a soft rubber tube already threaded behind the stomach. Once the clip is in place it is fastened by means of a screw through its clasp. The surgeon is in control of the tension applied to the stomach.

The requirements for clip 100 are the following:

1) It must be rigid enough to compress the two walls of the stomach to prevent leakage of food or fluid across the barrier created by the clip.

2) It must not be so tight as to cause necrosis of the stomach wall which could lead to ischemia and then perforation.

3) It must be coated with a biologically inert substance that would lessen the possibility of erosion into the stomach.

4) It must be additionally fastened to the stomach wall without the use of through and through staples so as to ensure against possible migration of the clip.

5) It must have a surface that will not encourage adhesions to surrounding organs.

6) The opening in the clip allowing food to pass from one chamber to another must be controlled.

Figures 16A, 16C:
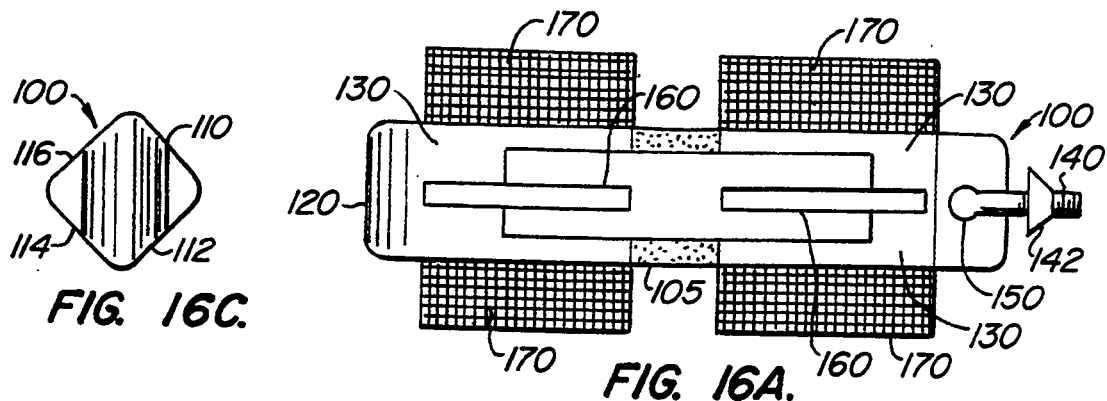
FIGS. 16A–16D are respective anterior, posterior, proximal, and distal views of the closed clamp utilized in the clamp banding procedure of this invention.
Figures 16B, 16D:
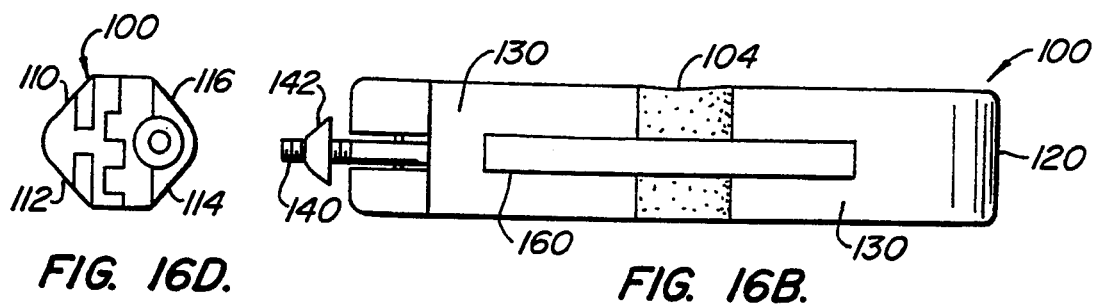
Figure 17:
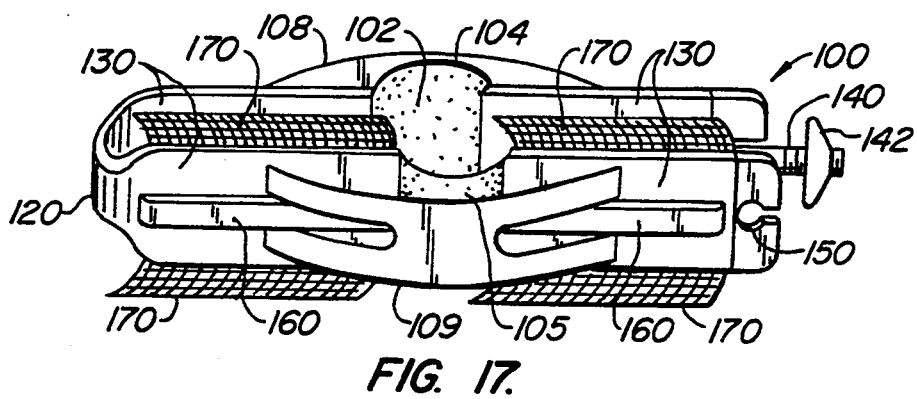
FIG. 17 is a posterior perspective view of the clamp shown in the closed position illustrating the opposed posterior and anterior portions of the clamp closed with the elastic arch portions medially of the clamp and the underlying woven mesh at the arch portions defining the required aperture of the stomach.
Figure 18:
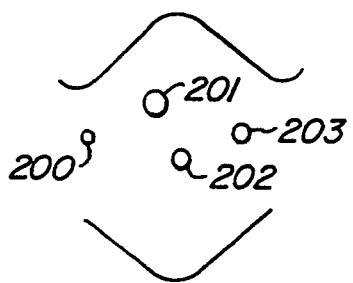
FIG. 18 is an anterior view of a patient's stomach illustrating locations of trocars for the clamp insertion procedure of this invention.
Figure 19:
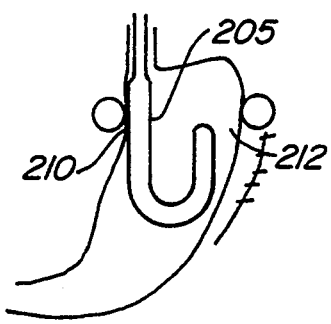
FIG. 19 is a schematic section of the stomach with an inserted Endo-Hand and illustrating on either side of the stomach the path around which the tube is inserted.
Figure 20:
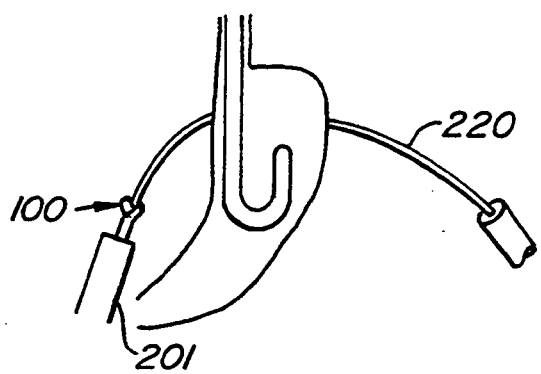
FIGS. 20 and 21 are schematics illustrating the tube drawing the clamp of this invention, posterior portion first, around the posterior portion of the patient's stomach.
Figure 21:
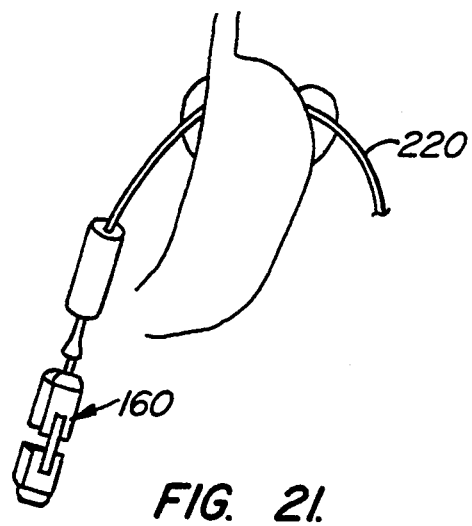
Figure 22:
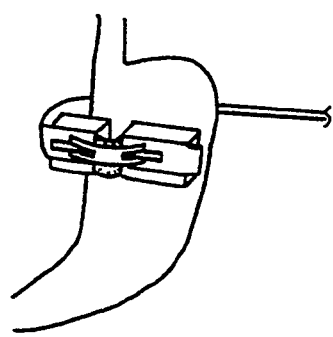
FIGS. 22 and 23 are schematics illustrating the closure of the anterior portion of the clamp over the stomach to roughly size the proximal pouch.
Figure 23:
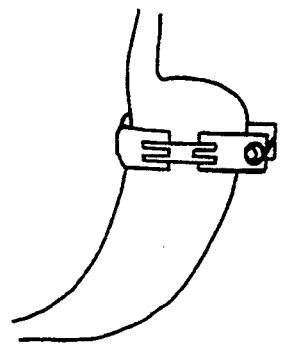
Figure 24:
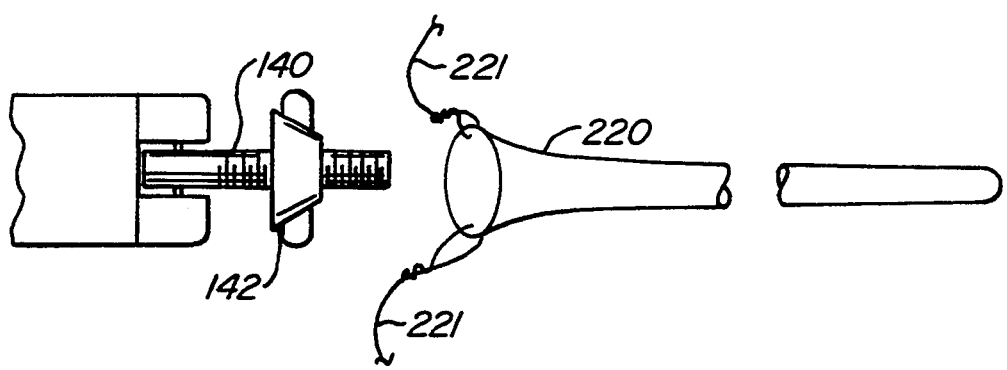
FIGS. 24 and 25 are details illustrating the attachment of the wing nut to the tube to enable the procedure of FIGS. 20 and 21.
Figure 25:
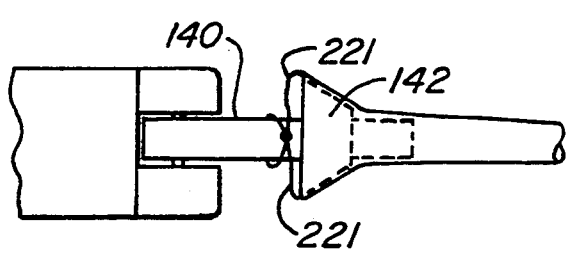
Figure 26:
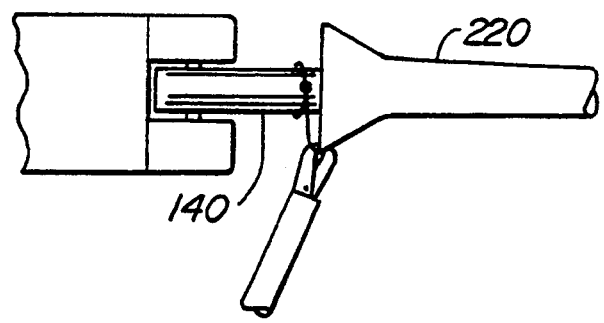
FIGS. 26 and 27 illustrates detachment of the wing nut from the tube by cutting of sutures connecting the tube and wing nut.
Figure 27:
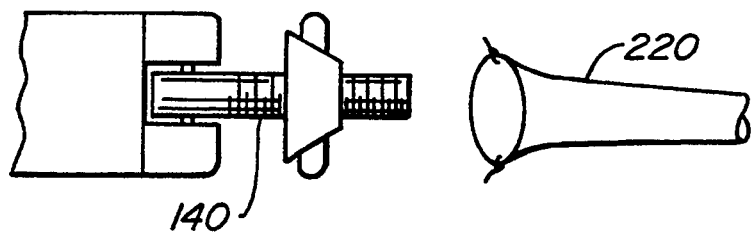
Figure 28:
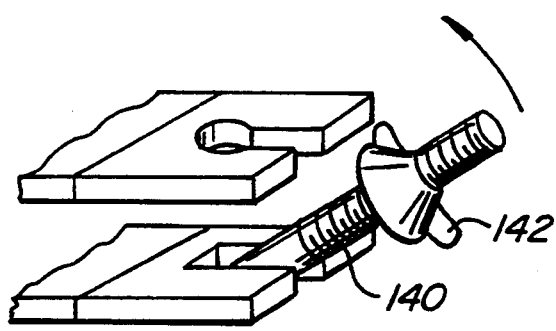
FIGS. 28 and 29 illustrate closure of the clamp.
Figure 29:
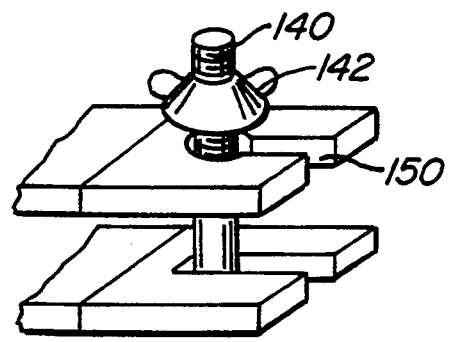
Figure 30:
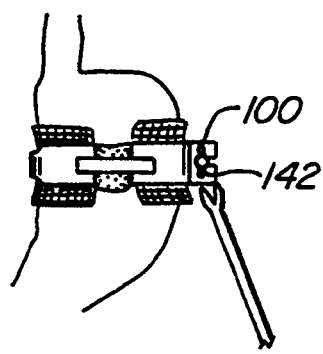
FIGS. 30 and 31 illustrate positioning of the clamp to define the required section of proximal pouch.
Figure 31:
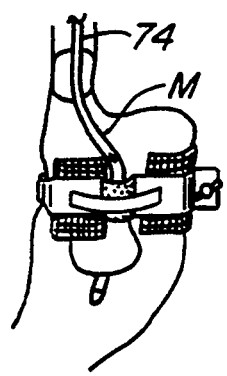
Figure 32:
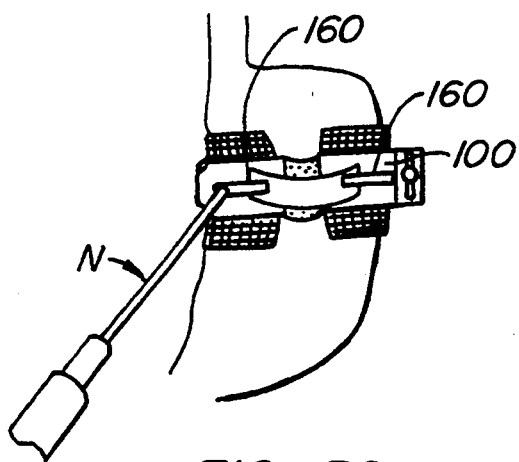
FIGS. 32–34 illustrate tightening of the clamp with arterial pulse measurement at the stomach wall to assure proper clamp tightening.
Figure 33:
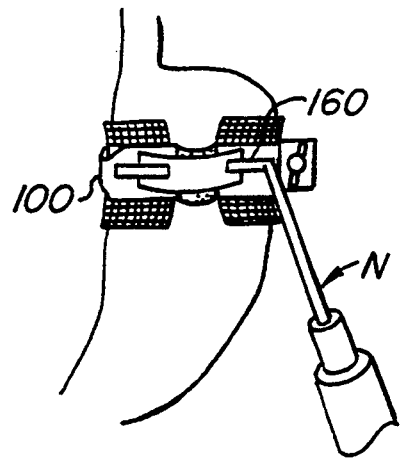
Figure 34:
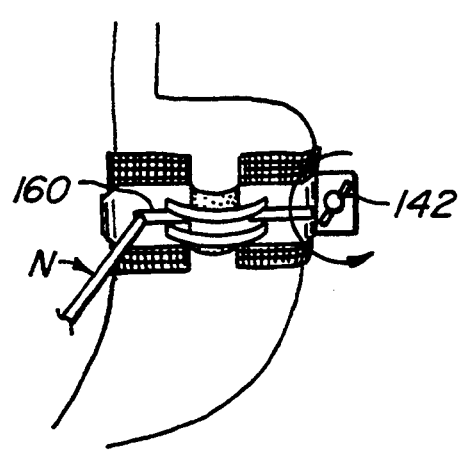
Figure 35:
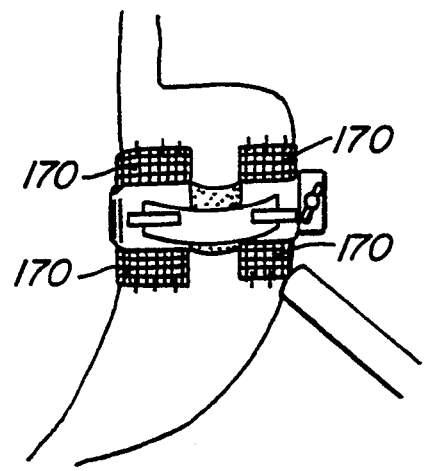
FIG. 35 illustrates stapling of the mesh on the anterior portion of the clamp to the anterior exposed portion of the stomach to prevent migration of the clamp.

Detailed construction of the clip 100 can be understood with respect to FIGS. 16A–16D, and 17. Its key features include:

1) 9–12 cm in length and one cm added for the clasp.
2) 10–12 mm in width.
3) 12–15 mm in depth when closed for passage down a 12 or 15 mm trocar.
4) The clip should have rounded edges so that it fits down a circular trocar—See FIGS. 16C and 16D and FIG. 17.

5) A hinge 120 is required for the side that will be placed on the lesser curvature side of the stomach.

6) Frames 130 consisting of flexible yet fairly rigid plastic for both sides of the clip.

7) Arches 108, 109 bridge the frame in the middle leaving an oval opening on both sides of the clip. This arch should also be of flexible plastic that is fairly rigid. This enables clip 100 to straighten when passed down a trocar, but will spring back into its arch shape upon arriving inside the peritoneal cavity.

8) Attached to the frame of each jaw of the clip in the middle are segments of woven mesh 104, 105. This mesh bridges the gap between the two straight segments 130 of the jaws and lies directly under the plastic arches 108, 109 that provide rigidity to the whole clip. The arches of plastic 108, 109 connecting the two straight elements 130 of the frame on either side of this opening 102 accommodate the mesh 104, 105 when it is fully expanded.

9) Covering each jaw on both inner and outer sides will be a thin piece of solid Gore-tex ™. The struts of the arch will also be covered with Gore-tex ™. This material prevents adhesion of the clamp 100 to adjacent organs.

10) The posterior jaw has a protruding thread screw 140 with a wing nut 142 attached to it. Its design allows the fastening of a rubber tube. The tube can be removed intraperitoneally without difficulty.

13) This protruding thread screw 140 is on a hinge 144. Once the rubber tube is removed, it can be flipped up using a standard grasper to lie 90 degrees to the plane of the jaw.

14) The anterior clamp has a clasp 150 on the end of it to receive this upright screw through an opening of clasp 150. The clasp 150 at its corners should be rounded so as to not present any sharp edges to the patient's tissue.

15) There are slots 160 in the middle of the anterior jaw 2 mm wide running the length of the device. A linear segment of the anterior stomach wall that is clamped in the clip will be exposed through this slot along its entire length except for where the mesh for the opening between chambers resides. This slot can be used to assess the blood flow in the crushed segment of the stomach wall.

11) Attached to the superior and inferior aspects of the anterior jaw and extending beyond for a distance of one cm are four segments of woven mesh material 170 such as Marlex ™. Affixing these segments of mesh to the anterior gastric wall by means of a standard laparoscopic stapling device such as is used in hernia repairs will prevent the clip 100 from migrating.

Having described the overall construction of the clip, the procedure in which the clip is utilized may now be described.

1) The patient is anaesthetized and placed supine on the operating table in a slightly head up position.

2) Ports 200–203 are placed in the positions indicated and are respectively for optic fiber (200), 12 mm trocar 201, and 10 mm trocars 202 and 203.

3) Endo-Hand 205 is inserted into the patient's stomach S and a 2–3 cm section high on the lesser curvature is cleared away from its mesentery at 210. The nerves of Laterjet will be excluded and the dissection will hug the stomach wall.

4) A corresponding area of similar length is cleared of blood vessels on the greater curvature 212.

5) Endo-Hand 205 is used to lift the stomach up toward the anterior abdominal wall. This maneuver will open the lesser sac. A rubber tube 220 is introduced through the lateral port and then is passed behind the stomach from the greater curvature side and is brought out the small opening on the lesser curvature side. See FIG. 20. Endo-Hand 205 is withdrawn.

6) The tube is then brought out through a 12 mm trocar 201 and affixed to the screw-thread protuberance jutting out from the end of the posterior jaw of clip 100. This maneuver is completed outside the patient. (See detail FIGS. 24 and 25). Specifically, sutures 221 tie to wing nut 142 from the end of tube 220 as shown.

7) The rubber tube 220 with clip 100 attached then draws the device into the trocar 201 by pulling on its other end which is outside the patient exiting form a different trocar (i.e. 203). The clip 100 in the closed position, is aided in this maneuver by advancing it down the trocar using a pusher bar.

8) Once clip 100 is inside the abdomen, traction continues on the rubber tube which guides the posterior jaw of the clip into the slot created behind the stomach. A grasper through the other port facilitates (202) this maneuver.

9) The smooth surface of the inner jaws of the clip that are lined with Gore-tex TM facilitate the positioning of the clip.

10) The rubber tube is disconnected from the protuberance. (See detail FIGS. 25 and 26).

11) The protruding thread screw 140 with its wing nut 142 attached is then flipped up by means of a grasper to an upright position. (See FIGS. 28, 29) It is then guided into the slot 150 on the anterior clasp that is designed to receive it. The jaws of the clip 100 need to be torqued slightly to carry out this maneuver, but when the upright screw thread 140 falls into the off center rounded slot at the end of the slot, the jaws of the clip 100 will be properly aligned.

12-13) The wing nut is turned on the threads a few turns so that the stomach is secured lightly in its jaws. (See FIG. 30).

14) At this point, a special tube M will be inserted down the patient's esophagus and will pass through the opening in the clip so that its tip is in the larger chamber of the stomach. (See tube 74, FIG. 3) A balloon 80 on its end is inflated and the tube pulled back until the opening 102 through the clip 100 is sealed. A second balloon 84 more proximal and in the distal esophagus is now inflated thus sealing off the proximal stomach chamber. A port 90 in the side of the tube between the two balloons is now injected with saline. The surgeon will observe the proximal stomach fill with fluid and can measure or approximate the size and volume of the pouch. Should the pouch be too large or too small the surgeon can move clip 100 proximally or distally to adjust the size of the proximal stomach pouch.

15) A sensor N measuring blood flow attached to a 5 mm rod will be then introduced down a trocar. This can either be an ultrasonic device or a laparoscopic adapted instrument that can be attached to the standard blood flow/oxygenation sensing device taped to the fingertip of patient by the anesthesiologist. Such a device, (manufactured by Nellcor Corp. Hayward, Calif.) is a common appliance found in virtually every operating room. It reads the patient's pulse and oxygenation saturation using light to record the degree of blood flow by the redness of the tissues. A sensing device utilizing the same principle attached to the end of a laparoscopic instrument would be placed in contact with the anterior stomach wall. A series of readings could be easily taken along the length of exposed in the slots 160 in the anterior jaw of the clip 100. This maneuver would determine the state of the blood flow in the crushed portion of the stomach.

16) Using the sensor device, the wing nut 142 is now gradually tightened. This maneuver closes the jaws of the clip 100 which in turn compresses the anterior and posterior walls of the stomach.

17) As the stomach walls are compressed within the jaws of the clip, the surgeon observes the sensor and tightens the wing nut until the sensor registers no flow. Then the surgeon backs off the wing nut 142 until flow returns. This maneuver ensures that the clip will be tight enough to prevent leakage across the clip, but not so tight that the walls of the stomach are deprived of their blood supply.

18) The mesh fringes 170 extending beyond the anterior jaw's superior and inferior margins are now smoothed out to lie flat upon the anterior surface of the stomach. Staples from a hernia stapler are then used to further affix the clip to the stomach by placing them into the Marlex TM mesh that extends from the frame of the clip.

19) The instruments are withdrawn and the trocar sites are closed. The patient can be fed that night and most likely can be discharged the next day.

The advantages of clip 100 are present. It will be relatively inexpensive to produce. Its size and design will allow it to be used in a laparoscopic morbid obesity operation which in turn will bring about a significant reduction in operative morbidity. In addition, by not using the staple technology to define the aperture of the stomach, issues of loss of the newly defined aperture are negated.

The concern over necrosis of the stomach wall by a compressing external device can be assuaged by the use of blood flow sensors. Ulcer formation should not be a problem because of the technique of the measurement of the blood flow and the tightening of the clip 100. The two surfaces of the stomach that are compressed against each other should atrophy over time from the pressure and the acid producing cells should no longer function. The clip will not interfere with the blood or nerve supply to the stomach. The staples affixing the mesh to the stomach should prevent the clip from migrating. Weight loss should be significant. Should the necessity arise that the operation be reversed, this can be easily accomplished by removing the clip. This too can be accomplished laparoscopically.

Clip 100 has a non penetrating feature making it a gastric non invasive procedure because the stomach's mucosa is never exposed. Unlike the VBG and the Gastric Bypass, there are no suture lines to disrupt or leak. There are no anastomotic lines to worry about and the clip 100 is relatively simple.

Although the foregoing invention has been described in some detail by way of illustration and example, for purposes of clarity of understanding, it will be obvious that certain changes and modifications may be practiced within the scope of the appended claims.

What is claimed is:

1. A method for performing laparoscopic gastroplasty on a patient, said method comprising:
   percutaneously introducing a plurality of trocars through the patient's abdominal wall;
   visualizing the patient's stomach using a laparoscope disposed in one of the trocars;

manipulating the stomach to expose the lesser curvature, anterior, and posterior walls of the stomach to the laparoscope;

dissecting the stomach from the mesentery along the lesser and greater curvatures dividing the stomach along a line into a proximal pouch adjacent the esophagus and a distal region;

introducing a banding device for encircling the stomach along a dissecting line for defining the proximal pouch, the distal region with an aperture defined between the proximal pouch and the distal region;

introducing a nasogastric tube into the stomach so that it passes through the aperture;

inflating a first balloon on the nasogastric tube distally of the aperture and a second balloon in the esophagus, to seal the proximal pouch in the stomach;

introducing a measured volume of fluid into the proximal pouch through the nasogastric tube until the pouch is filled;

repositioning the banding device and reintroducing fluid until the position of the banding device provides a preselected fluid volume upon filling; and closing the banding device over the stomach along a line defined by the aperture in the band at its final position, with a passage between the proximal pouch and distal region of the stomach being defined by the aperture.

2. A method for performing laparoscopic gastroplasty on a patient according to claim 1 and wherein said introducing of said banding device includes:

introducing a band having staples thereon with a portion of said band defining said aperture;

and, said closing step includes:

closing said staples on said band to define said aperture with said band and fastening the distal ends of said band with said staples across said stomach.

3. A method for performing laparoscopic gastroplasty on a patient according to claim 1 and wherein said introduction of said banding device includes:

introducing a clip having opposed portions thereon with said opposed portions each defining portions of said aperture;

and said closing step includes:

closing said clip about said stomach to define a proximal pouch to said stomach.

4. A method for performing laparoscopic gastroplasty on a patient according to claim 3 and including the steps of:

fastening mesh to said banding device, and, stapling said mesh to at least one wall of said stomach to insure against migration of said banding device.

5. A method for performing laparoscopic gastroplasty on a patient according to claim 1 and including the further step of:

examining the arterial blood flow of said stomach during closing of said banding device.

6. A method for performing laparoscopic gastroplasty on a patient according to claim 1 and wherein said introducing step includes:

laparoscopically passing a member from the anterior of said patient around the posterior of said stomach and threading said member exterior of said patient;

attaching a banding device to said exteriorly threaded member;

drawing said banding device interiorly of said patient utilizing said member to lodge a portion of said device posterior of said stomach; and, fastening said banding device over said stomach.

* * * * *